United States Patent [19]

Bieringer et al.

[11] Patent Number: 4,692,181
[45] Date of Patent: Sep. 8, 1987

[54] HERBICIDAL COMPOSITIONS

[75] Inventors: Hermann Bieringer; Friedhelm Schwerdtle, both of Eppstein, Fed. Rep. of Germany

[73] Assignee: Hoechst Aktiengesellschaft, Frankfurt am Main, Fed. Rep. of Germany

[21] Appl. No.: 341,803

[22] Filed: Jan. 22, 1982

Related U.S. Application Data

[63] Continuation of Ser. No. 72,934, Sep. 6, 1979, abandoned.

[30] Foreign Application Priority Data

Sep. 8, 1978 [DE] Fed. Rep. of Germany ....... 2839087

[51] Int. Cl.⁴ .............................................. A01M 57/12
[52] U.S. Cl. .......................................... 71/86; 71/73; 71/116; 71/117; 71/120
[58] Field of Search ...................................... 71/86, 93

[56] References Cited

U.S. PATENT DOCUMENTS 4,168,963  9/1979  Rupp et al. ............................ 71/86

Primary Examiner—Catherine L. Mills
Attorney, Agent, or Firm—Curtis, Morris & Safford

[57] ABSTRACT

Herbicidal compositions containing as active substance a combination of at least two of the following components:

(A) phosphinotricine or a derivative thereof of the formula

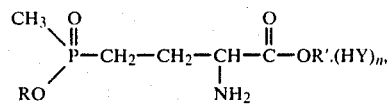

(B) a phenoxy-alkane-carboxylic acid of the formula

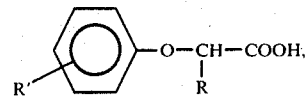

(C) a phenylurea derivative of the formula

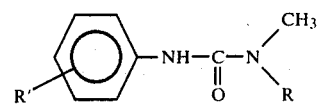

and
(D) a s-triazine derivative of the formula

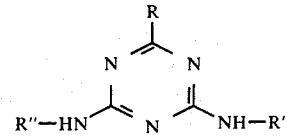

in a proportion by weight of compound A to compounds B, C, and D, preferably in the range of from 4:1 to 1:30, exhibit a synergistic herbicidal effect.

7 Claims, No Drawings

HERBICIDAL COMPOSITIONS

This is a continuation of application Ser. No. 72,934, filed Sept. 6, 1979, now abandoned.

The present invention relates to combinations of herbicidally effective substances of the group of phosphinotricines with active substances of the group of phenoxyalkane-carboxylic acids and phenyl urea and triazine derivatives.

Recently, combinations of pesticides have increased in importance and especially in the case of synergistic combinations. Valuable pesticides can be prepared and applied in relatively small amounts which exhibit specially desired effects, such as selectively or broad range effect, rapid action or long lasting effect and so on.

It is known that growth herbicides of the group of phenoxy-alkanecarboxylic acids (compounds of the type B below) effectively combat in the first place broad-leaved weeds, while they are little effective only against weed grasses. This is the reason why compounds of this type are suitable for application in cultivations of monocotyledoneae such as cereals and rice.

Urea derivatives (compounds of the type C below) and triazine derivatives (compounds of the type D below) are known to act, above all, on germinating dioctyledonous weeds and to a very small extent only on monocotyledonous plants, while they are hardly effective against plants that have germinated and further grown. In the latter case the aforesaid substances would have to be used in very high doses as they are insufficiently taken up by the leaves and, consequently, are not transported to the point of action in the plant (cf. W. Koch and K. Hurle, Grundalgen der Unkrautbekämpfung, edited by Eugen Ulmer, Stuttgart 1977).

In contradistinction thereto, the recently discovered herbicides of the group of phosphinotricines (compounds of the type A below) are characterized by a pronounced leaf absorption and contact effect and they combat weeds of all botanic classes. Consequently, they can be used for the non selective control of undesired plant growth on agricultural areas, industrial sites and the like (cf. DE-OS No. 2,717,440).

It has now been found, surprisingly, that mixtures of the above specified compounds have a pronounced synergistic effect against weeds. The synergism makes it possible considerably to reduce the applied amounts of the individual herbicides. Moreover, special advantageous effects have been found, for example an improved permanent effect of the combination or an accelerated effect.

It is therefore, the object of the present invention to provide herbicidal compositions containing as active substance a combination of at least two of the following components:

(A) phosphinotricine or a derivative thereof of the formula

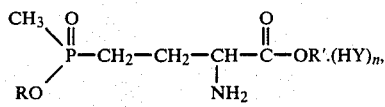

[cf. DE-OS No. 27 17 440] in which
R denotes H, R' denotes H and n is zero (A I) or
R denotes H, R' denotes H, Y denotes Cl and n is 1 (A II), or
R denotes H, R' denotes $C_1$-$C_4$alkyl and n is zero (A III) or
R denotes $NH_4$, R' denotes H and n is zero (A IV) or
R denotes Na or K, R' denotes H, Na or K and n is zero (A V), (B) a hormone weed killer of the group of phenoxyalkanecarboxylic acids of the formula

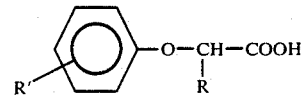

in which R denotes H and R' denotes 2,4-dichloro (B I) 2,4-dichlorophenoxyacetic acid (cf. Contr. Boyce Thompson Inst. Pl. Res. 12, page 321 (1942)) or
R denotes H and R' denotes 2,4,5-trichloro (B II) 2,4,5-trichlorophenoxyacetic acid or butoxone (cf. Science 100, page 154 (1944)) or
R denotes H and R' denotes 2-methyl-4-chloro (B III) 2-methyl-4-chlorophenoxyacetic acid or metaxone (cf. Nature 155, page 498 (1945)) or
R denotes $CH_3$ and R' denotes 2-methyl-4-chloro (B IV) 2-(2-methyl-4-chlorophenoxy)-propionic acid or mecoprop (cf. Ann. Appl. Biol. 40, page 232 (1953)) or
R denotes $CH_3$ and R' denotes 2,4-dichloro (B V) 2-(2,4-dichlorophenoxy)-propionic acid or dichloroprop (cf. Proc. Am. Soc. hort. Sci. 45, page 353 (1944)), (C) a phenylurea derivative of the formula

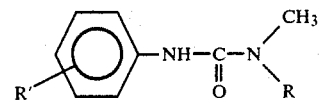

in which R denotes $CH_3$ and R' denotes 4-chloro (C I) N-(4-chlorophenyl)-N',N'-dimethyl urea or monuron (cf. Science 114, page 493 (1951)) or
R denotes $CH_3$ and R' denotes 3,4-dichloro (C II) N-(3,4-dichlorophenyl)-N',N'-dimethyl urea or diuron (cf. Science 114, page 493 (1951)) or
R denotes $OCH_3$ and R' denotes 4-chloro (C III) N-(4-chlorophenyl)-N'-methoxy-N'-methyl urea or monolinuron (cf. Meded. Landb. Hoogesch. Opzoek Stns. Gent 27, page 1275 (1962)) or
R denotes $OCH_3$ and R' denotes 3,4-dichloro (C IV) N-(3,4-dichlorophenyl)-N'-methoxy-N'-methyl urea or linuron (cf. Meded. Landb. Hoogesch., Gent, 27, page 1275 (1962)), and
(D) a s-triazine derivative of the formula

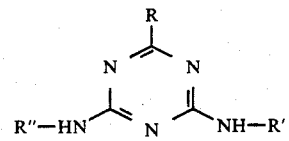

in which
R denotes Cl, R' denotes i-$C_3H_7$ and R" denotes $C_2H_5$ (D I) 4-ethylamino-2-chloro-6-isopropylamino-s-triazine or atrazine (cf. Proc. IV Int. Congr. Crop Prot. Hamburg 1957) or R denotes Cl, R' denotes C$_2$H$_5$ and R" denotes C$_2$H$_5$ (D II) 4,6-diethylamino-2-chloro-s-triazine or simazine (cf. Experienta 12, page 146 (1956)) or R denotes Cl, R' denotes C$_2$H$_5$ and R" denotes t-C$_4$H$_9$ (D III) 4-ethylamino-6-t.butylamino-2-chloro-s-triazine or terbutylazine (cf. Proc. 8th Br. Weed Contr. Conf. 1966, page 485) or R denotes SCH$_3$, R' denotes C$_2$H$_5$ and R" denotes i-C$_3$H$_7$ (D IV) 4-ethylamino-6-isopropylamino-2-methylthio-s-triazine or ametryne (Adv. Pest. Control Res., 3, page 289 (1960)) or R denotes SCH$_3$, R' denotes i-C$_3$H$_7$ and R" denotes i-C$_3$H$_7$ (D V) 4,6-diisopropylamino-2-methylthio-s-triazine or prometryne (cf. Chemy. Ind. 1393 (1962)) or R denotes OCH$_3$, R' denotes C$_2$H$_5$ and R" denotes t-C$_4$H$_9$ (D VI) 4-ethylamino-6-t.butylamino-2-methoxy-s-triazine or terbumeton (cf. Proc. 8th Br. Weed Control Conf. 1966, page 485).

The mixing proportions of components A to B, C or D can vary within wide limits, approximately between 4:1 to 1:30. The mixing proportion depends on the type of the components used, the state of development of the weeds, the weed spectrum and so on. Mixing proportions of from 2:1 to 1:20 are preferred.

Preferred herbicidal combinations are those of component A with components B, C or D. Combinations of component A with components B and C or B and D or C and D or B and C and D are also possible.

The combinations according to the invention can be used in the form of mixed formulations of the individual components, for example as wettable powders or emulsion concentrates, which are diluted with water in the usual manner prior to application. Alternatively, the individual components can be formulated separately in the usual manner and then commonly diluted with water as so-called tank mixtures.

In general, the herbicide of type A is applied in an amount of from 0.5 to 3.0 kg per hectare, components B, C or D are applied in an amount of from 0.25 to 10.0 kg/ha, that is to say the total amount applied of the herbicidal combination is in the range of from about 0.75 to 13 kg per hectare.

The compositions according to the invention can be commercialized in the usual formulations known to the expert, for example as wettable powders, emulsifiable concentrates or sprayable solutions. The formulations generally contain from 2 to 95% by weight of the combination of active substances.

Wettable powders are formulations which are uniformly dispersible in water and which, in addition to the active compounds and a diluent or inert material, also contain wetting agents, for example, polyoxethylated alkylphenols, polyoxethylated oleylamines or stearylamines, alkylsulfonates or alkylphenylsulfonates and dispersing agents, for example sodium ligninsulfonate, sodium-dinaphthylmethane-disulfonate, or the sodium salt of oleoylmethyl taurine.

Emulsifiable concentrates are obtained by dissolving the mixture of active compounds in an organic solvent, for example, butanol, cyclohexanone, dimethyl formamide, xylene or even higher boiling aromatics, and adding an emulsifier, for example, a polyoxethylated alkylphenol or a polyoxethylated oleylamine or stearylamine.

In the herbicidal compositions the concentrations of the active compounds in the commercial formulations may vary. In wettable powders, the active compound concentration varies, for example, between about 10 and 95%, the remainder consisting of the abovementioned formulation additives. In the case of emulsifiable concentrates, the active compound concentration is about 10% to 80%. Dust formulations usually contain 5–20% of active compound, and sprayable solutions about 2–20%. In the case of granules, the active compound content in part depends on whether the active compound is in a liquid or solid form and what granulating auxiliaries, fillers and the like are used.

The commercial concentrates are diluted prior to application in the usual manner, for example by means of water in the case of wettable powders and emulsifiable concentrates. Dusts, granules and sprayable solutions need not be diluted with further inert material prior to use. The amount of active ingredients necessary for obtaining the desired result depends on external conditions such as temperature, humidity and the like.

The compositions according to the invention can be combined with other herbicides, fungicides and insecticides.

The following examples illustrate the invention.

EXAMPLES OF FORMULATION

EXAMPLE 1

A wettable power (WP) of component A IV and component C II is prepared.

| Proportion of A IV:C II (in % by weight) | 1:5 | 1:3 | 1:8 |
| --- | --- | --- | --- |
| A IV | 8 | 12 | 6 |
| C II | 40 | 36 | 48 |
| synthetic silicic acid | 37.5 | 38.5 | 31.5 |
| sodium dinaphthylmethane disulfonate | 8 | 8 | 8 |
| sodium alkylnaphthalene sulfonate | 6 | 5 | 6 |
| natrium stearate | 0.5 | 0.5 | 0.5 |
| | 100 | 100 | 100 |

EXAMPLE 2

A wettable powder of component A IV and component C IV is prepared.

| Proportion of A IV:C IV (in % by weight) | 1:5 | 1:3 |
| --- | --- | --- |
| A IV | 8 | 12 |
| C IV | 40 | 36 |
| sodium ligninsulfonate | 10 | 10 |
| sodium oleoyl-N—methyltaurine | 1 | 1.5 |
| sodium stearate | 0.5 | 0.5 |
| sodium alkylnaphthalene sulfonate | 2 | 2.5 |
| synthetic silicic acid | 35.5 | 34.5 |
| sodium bicarbonate | 3 | 3 |
| | 100 | 100 |

EXAMPLE 3

A wettable powder of component A IV and D I is prepared.

| Proportion of A IV:D I (in % by weight) | 1:5 | 1:3 |
| --- | --- | --- |
| A IV | 10 | 15 |
| D I | 50 | 45 |
| sodium sulfate | 5 | 5 |
| sodium dodecylbenzene sulfonate | 1 | 0.5 |

-continued

| | | |
|---|---|---|
| Proportion of A IV:D I (in % by weight) | 1:5 | 1:3 |
| sodium stearate | 0.5 | 0.5 |
| sodium ligninsulfonate | 12 | 14 |
| kaolin | 21.5 | 20 |
| | 100.0 | 100.0 |

EXAMPLE 4

A wettable powder is prepared from component A IV and component D IV with the additives as defined in Example 3.

EXAMPLE 5

A wettable powder is prepared from components A IV and B II or B IV.

| Proportion (in % by weight) | A IV:B II = 1:2 | A IV:B IV = 1:2 |
|---|---|---|
| A IV | 20 | 20 |
| B II (Na—salt) | 43.4 | — |
| B IV (Na—salt) | — | 44.1 |
| sodium alkylnaphthalene disulfonate | 2 | 4 |
| sodium dinaphthalene methane disulfonate | 6 | 5 |
| sodium oleoyl-N—methyltaurine | 0.5 | 0.5 |
| sodium bicarbonate | 4 | 4 |
| diatomaceous earth | 10 | 10 |
| synthetic silicic acid | 14.1 | 12.4 |
| | 100.0 | 100.0 |

To prepare the wettable powders the components were mixed and finely milled once in a cross beater mill and then twice in a pinned disk mill.

BIOLOGICAL EXAMPLES

EXAMPLE I

Perennial weed grasses (Cynodon and Paspalum) were grown from rhizomes in pots in the greenhouse. When the plants had reached a height of 10 to 15 cm, they were sprayed with the herbicides (post-emergence process). Approximately 4 weeks after the treatment the results were evaluated in % by visual inspection of the plants which had been kept in the greenhouse. It was found that the herbicidal effect of the combination according to the invention was far beyond the effect to be expected in view of the individual effects of the mixing components. Thus, the combination had a considerable synergistic effect.

TABLE I

Treatment of perennial weed grasses in the post-emergence process in the greenhouse (destruction in %)

| | dose kg AS/ha | Cynodon dactylon | Paspalum conjugatum |
|---|---|---|---|
| A II 25% sprayable solution | 1.44 | 0 | 86 |
| | 2.88 | 40 | — |
| C II WP 80% | 1.00 | 24 | 16 |
| A II + C II | 1.44 + 1.0 | 55 | 100 |
| | 2.88 + 1.0 | 95 | — |
| AS active substance amount of water applied 4 repetitions evaluation 4 weeks after treatment | 800 liter per hectare | | |

EXAMPLE II

In the open field an area on which various types of weeds were growing was selected for a small lot experiment. The herbicides were sprayed by a post-emergence process to the lots each having a size of 10 square meters using water in an amount of 600 liters per hectare. The experiment was repeated twice. 27 days after the treatment the herbicidal effect was evaluated in % by visual inspection (Table II). It was found, surprisingly, that the herbicidal combinations according to the invention had a pronounced synergistic effect above the additive effect of the individual components.

TABLE II

Weed control, field trial by post-emergence process
% destruction, evaluation 27 days after treatment

| | dose kg AS/ha | Lolium perennial | Echinochloa crus galli | Poa annua |
|---|---|---|---|---|
| A II 18% sprayable solution | 0.75 | 33 | 49 | 49 |
| B IV | 2.0 | 0 | 0 | 0 |
| B II | 2.0 | 0 | 0 | 0 |
| A II + B IV | 0.75 + 2.0 | 90 | 85 | 88 |
| A II + B II | 0.75 + 2.0 | 97 | 90 | — |
| amount of water applied | 600 liters per hectare | | | |
| size of lot | 10 square meters | | | |
| 2 repetitions | | | | |

EXAMPLE III

In the field small lots infested with couch grass were treated with herbicides when the grass (*Agropyron repens*) had reached the three-leaf stage. 600 liters of water were sprayed per hectare, the lots had a size of 10 square meters each and the experiment was repeated twice. The destruction was evaluated in % by visual inspection 15 days and 58 days after the treatment. It was found that at the early evaluation 15 days after application the herbicidal combinations exhibited approximately a normal herbicidal effect as could be expected in view of the additive effect of the individual components. At the later evaluation, i.e. 58 days after application, the herbicidal combinations still had a good effect while the effect of the individual components was no longer satisfactory. Hence, the combinations had a synergistic effect over a prolonged period of time which is rather valuable in that the destruction of couch grass is economically important and in this manner a permanent control of couch grass can be achieved with the herbicidal combinations according to the invention.

TABLE III

Control of couch grass (*Agropyron repens*) in a field trial by a post-emergence process. The destruction is indicated in % for 2 evaluation terms

| | dose kg AS/ha | Agropyron repens % destruction after | |
|---|---|---|---|
| | | 15 days | 58 days |
| A II 18% sprayable solution | 1.0 | 90 | 33 |
| C II WP 80 | 3.2 | 0 | 33 |
| D I WP 50 | 3.0 | 17 | 33 |
| A II + C II | 1.0 + 3.2 | 87 | 85 |
| A II + D I | 1.0 + 3.0 | 90 | 98 |
| Evaluation stages of couch grass | start of tillering (15 days after treatment) start of shooting (58 days after treatment) | | |
| amount of water applied | 600 liters per hectare | | |

TABLE III-continued

Control of couch grass (*Agropyron repens*) in a
field trial by a post-emergence process. The
destruction is indicated in % for 2 evaluation terms

| | dose | *Agropyron repens* % destruction after | |
|---|---|---|---|
| | kg AS/ha | 15 days | 58 days |
| size of lot | | 10 square meters | |
| 2 repetitions | | | |

What is claimed is:

1. A herbicidal composition containing as an active ingredient, herbicidally effective amounts of compound A and compound B, wherein compound A has the formula

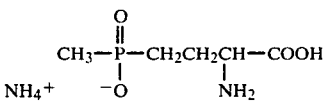

and compound B has the formula

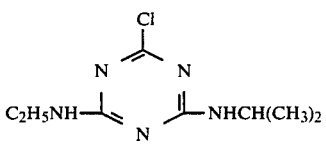

wherein the proportion by weight of compound A to compound B is in the range of from 1:1.5 to 1:4.

2. A herbicidal composition containing as an active ingredient, herbicidally effective amounts of compound A and compound B, wherein compound A has the formula

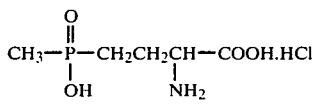

and compound B has the formula

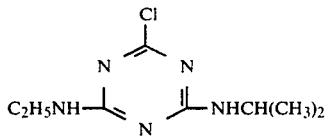

wherein the proportion by weight of compound A to compound B is in the range of from 1:1.5 to 1:4.

3. A herbicidal composition which comprises from 2 to 95% by weight of the active ingredient as defined in claim 1 in admixture with up to 98% by weight of an inert material.

4. Method for combatting weeds which comprises applying to the infested area an effective amount of a herbicidal composition as defined in claim 1.

5. Method for combatting weeds which comprises applying to the infested area 0.75 to 13 kg per hectare of a herbicidal composition as defined in claim 1.

6. A herbicidal composition which comprises from 2 to 95% by weight of the active ingredient as defined in claim 2 in admixture with up to 98 percent by weight of an inert material.

7. Method for combating weeds which comprising applying to the infested area an effective amount of a herbicidal composition as defined in claim 6.

* * * * *